(12) United States Patent
Giurgiutiu et al.

(10) Patent No.: US 7,174,255 B2
(45) Date of Patent: Feb. 6, 2007

(54) SELF-PROCESSING INTEGRATED DAMAGE ASSESSMENT SENSOR FOR STRUCTURAL HEALTH MONITORING

(75) Inventors: Victor Giurgiutiu, Columbia, SC (US); Buli Xu, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 10/987,765

(22) Filed: Nov. 12, 2004

(65) Prior Publication Data
US 2005/0114045 A1 May 26, 2005

Related U.S. Application Data

(60) Provisional application No. 60/519,469, filed on Nov. 12, 2003.

(51) Int. Cl.
G01H 11/08 (2006.01)
G01R 31/08 (2006.01)

(52) U.S. Cl. .......................... 702/35; 324/524

(58) Field of Classification Search ................ 702/56, 702/34–38; 324/525; 73/147
See application file for complete search history.

(56) References Cited

U.S. PATENT DOCUMENTS

| | | | | |
|---|---|---|---|---|
| 2,440,198 A * | 4/1948 | Green | ................ | 73/147 |
| 3,713,127 A * | 1/1973 | Keledy et al. | ............... | 340/540 |
| 4,821,575 A * | 4/1989 | Fujikake et al. | .............. | 73/626 |
| 4,995,260 A * | 2/1991 | Deason et al. | ................ | 73/632 |
| 5,167,157 A * | 12/1992 | Wertz et al. | ................... | 73/627 |
| 5,814,729 A * | 9/1998 | Wu et al. | ..................... | 73/588 |
| 6,006,163 A * | 12/1999 | Lichtenwalner et al. | ...... | 702/36 |
| 6,768,312 B2 * | 7/2004 | Sun et al. | .................... | 324/525 |
| 2003/0009300 A1 * | 1/2003 | Giurgiutiu | .................... | 702/35 |

OTHER PUBLICATIONS

Giurgiutiu, et al., *Development of a Field-Portable Small-Size Impedance Analyzer for Structural Health Monitoring using the Electromechanical Impedance Technique*, SPIE's 11th Annual International Symposium on Smart Structures and Materials and 9th Annual International Symposium on NDE for Health Monitoring and Diagnostics, Mar. 14-18, 2004, San Diego, CA, paper #5391-92, (12 pages).

* cited by examiner

Primary Examiner—John Barlow
Assistant Examiner—Victor J. Taylor
(74) Attorney, Agent, or Firm—Dority & Manning, P.A.

(57) ABSTRACT

A small, lightweight, portable, and inexpensive self-processing integrated damage assessment sensor (SPIDAS) that may be temporarily or permanently attached to a structure for structural health monitoring is provided. The SPIDAS device employs an electromechanical impedance measuring method to directly measure the high-frequency local impedance spectrum of the structure, process the electromechanical impedance data, and issue structural health reports that the device may transmit over a wireless connection.

15 Claims, 6 Drawing Sheets

SELF-PROCESSING INTEGRATED DAMAGE ASSESSMENT SENSOR FOR STRUCTURAL HEALTH MONITORING

RELATED APPLICATIONS

The present application claims priority to U.S. Provisional Application Ser. No. 60/519,469, which was filed on Nov. 12, 2003.

GOVERNMENT INTERESTS

Support for research in connect with this invention has been provided by funding from Universal Technology Corporation under contract # 03-S470-033-C1 which is a part of Contract No. F33615-01-D-5801 awarded by the Air Force Research Laboratory (AFRL).

FIELD OF THE INVENTION

The presently disclosed technology relates to apparatuses and methodologies for monitoring the physical integrity or health of a structure. In particular, the presently disclosed technology relates to a self-processing integrated damage assessment sensor for structural health monitoring (SPI-DAS).

BACKGROUND OF THE INVENTION

Structural health monitoring (SHM) corresponds to methodologies for determining the health of a structure based on readings from one or more sensors embedded into the structure and monitored over time. Exemplary monitored structures may include buildings, bridges, dams, aircraft, and any other structures the physical integrity of which may be of significance to any interested parties.

Structural health monitoring may be conducted passively or actively. Passive SHM may be conducted by monitoring a number of parameters including, as non-limiting examples, loading stress, environmental action, performance indicators, and acoustic emissions from cracks or other sources. Inferences may then be made of the state of structural health from a structural model based on the monitored parameters. Active SHM may be conducted by performing proactive interrogation of the structure. The state of structural health may then be determined from an evaluation of detected parameters.

Both approaches perform a diagnosis of structural health and safety, to be followed by a prognosis of the remaining life of the structure. Passive SHM uses passive sensors that only "listen" but do not interact with the structure. Therefore, they do not provide direct measurement of damage presence and intensity. Active SHM uses active sensors that interact with the structure and thus determine the presence or absence of damage. Exemplary methods used with active SHM resemble methods of nondestructive evaluation (NDE) corresponding to ultrasonic testing and eddy current testing, except that they are used with embedded sensors. Hence, active SHM could be viewed as a method of embedded nondestructive evaluation.

One widely used active structural health monitoring method employs piezoelectric wafer active sensors (PWAS), which send and receive Lamb waves and may be used to determine the presence of cracks, delaminations, disbonds, and corrosion. Due to its similarities to nondestructive evaluation ultrasonics, this approach is also known as embedded ultrasonics. Although PWAS are small, unobtrusive, and inexpensive, the laboratory measurement equipment used, for example as a proof-of-concept demonstration of the present technology, is bulky, heavy, and relatively expensive. Such laboratory equipment cannot be easily transported into the field for on-site structural health monitoring. Therefore, such equipment is less desirable for large-scale deployment of the presently disclosed electromechanical (E/M) impedance technology for SHM applications.

Several investigators have explored means of reducing the size of the impedance analyzer, to make it more compact, and even field-portable. Alternative ways of measuring the E/M impedance, which are different from those used by the impedance analyzer, have also been considered. One approach as illustrated in FIG. 1 by Pardo de Vera and Guemes (1997), at the Polytechnic University of Madrid, Spain, employed an E/M impedance technique to detect damage in a composite specimen 12 by way of a piezoelectric sensor 14 using a simplified impedance measuring method corresponding to the use of an RC-bridge 10 instead of a laboratory impedance analyzer. Disadvantages associated with using the RC-bridge 10 included the fact that additional instrumentation and processing needed to be used to separate the signal into its real (in phase) and imaginary (out of phase) parts, and precise bridge balance needed to be initially attained in order to prevent the excitation signal from leaking into the output and masking the sensing signals.

In addition to the above, Peairs, Park and Inman (2002) suggested a method of generating impedance measurements utilizing an FFT analyzer 20 and small current measuring circuit 22 as illustrated in FIG. 2. The approximated impedance ($Z_{PZT}$) is: $Z_{PZT}=V_i/I$, where I is the current through the sensing resistor ($R_S$). Disadvantages associated with this method include the fact that $V_i$ is not the exact voltage across the PZT but rather is an approximation, so that there may be an unacceptable error for measured $Z_{PZT}$. In addition, the error will increase with frequency so that, at high frequencies of approximately 100 kHz for a gain of 20 dB with a standard 741-type integrated circuit operational amplifier, the amplifier becomes ineffective due to roll-off of the output signal. Finally, a large laboratory instrument-FFT analyzer is still needed.

While various implementations of nondestructive evaluation (NDE) devices have been developed, no design has emerged that generally encompasses all of the desired characteristics as hereafter presented in accordance with the subject technology.

SUMMARY OF THE INVENTION

In view of the recognized features encountered in the prior art and addressed by the present subject matter, an improved apparatus and methodology for structural health monitoring is disclosed directed toward providing a sensor device that makes use of a E/M impedance measuring methodology by embedding relatively small sensor devices within structures to be monitored.

In accordance with aspects of certain embodiments of the present subject matter, a PWAS may be temporarily or permanently attached to a structure to permit E/M impedance measurements to directly measure the high-frequency local impedance spectrum of the structure. Because the high-frequency local impedance spectrum is much more sensitive to incipient damage or anomalies than the low-frequency global impedance, the E/M impedance methodology in accordance with the present technology is better suited for applications in structural health monitoring than other more conventional methods.

In accordance with additional aspects of other embodiments of the present technology, a structure attachable sensor may be combined with other components that together provide a number of functionalities. These functionalities correspond to: measurement of the E/M impedance of a monitored structure; storage of a spectral database of historical data of E/M impedance spectra; analysis and decision through E/M impedance spectroscopy, comparison of measured data with stored data, issuance of structural health reports; and compaction and conditioning of structural health information for transmission over a wired or wireless network.

In accordance with yet additional aspects of the present technology, sensors incorporated within exemplary devices constructed in accordance with the present technology may correspond to the previously mentioned PWAS, or may correspond in other embodiments to resistive (R), capacitive (C), or combination resistive-capacitive (R-C) devices.

In accordance with still further aspects of the present technology, integrated electronics devices are provided in the form of self-processing integrated damage assessment sensors. One aspect of the present technology is to provide methodologies whereby selected functions of existing present-day bulky and expensive laboratory-size impedance analyzers may be provided as an integrated-circuit sized impedance analyzer that can be easily embedded into a structure for in-situ structural health measurement. A related aspect to this aspect of the present technology is the development of new implementation concepts utilizing state-of-the-art methods and technologies in on-chip data acquisition, processing, and data transmission.

In accordance with yet still further aspects of the present technology, implementation of the present technology will result in the seamless integration of active sensing, electronics, analysis, and diagnostics, into a compact system in an unobtrusive way. In addition, by developing a lost-cost miniaturized impedance-measuring device, an on-line SHM system would be more compact and more easily used by maintenance crews and SHM operators.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures).

Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
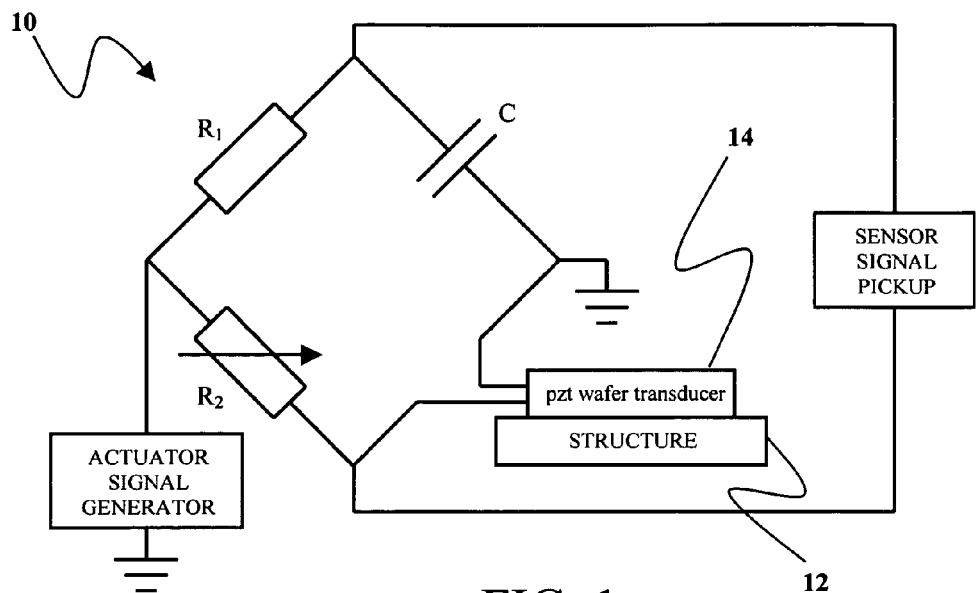
FIG. 1 illustrates a known RC bridge for detecting impedance changes of a PZT wafer transducer affixed to a monitored structure.
Figure 2:
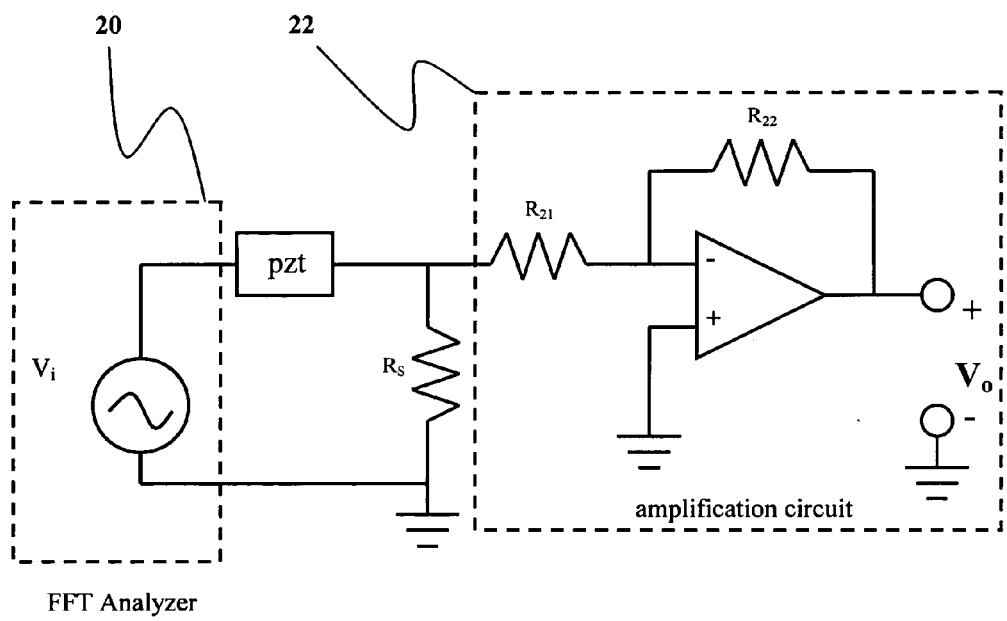
FIG. 2 illustrates an exemplary impedance approximating circuit including signal amplification.

Repeat use of reference characters throughout the present specification and appended drawings is intended to represent same or analogous features or elements of the invention.

DETAILED DESCRIPTION OF THE PREFERRED EMBODIMENTS

As discussed in the Summary of the Invention section, the present subject matter is particularly concerned with technology that makes use of electromechanical (E/M) impedance measuring apparatus and associated methodologies by providing relatively small sensor devices capable of being embedded within structures to be monitored.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

Figure 3:
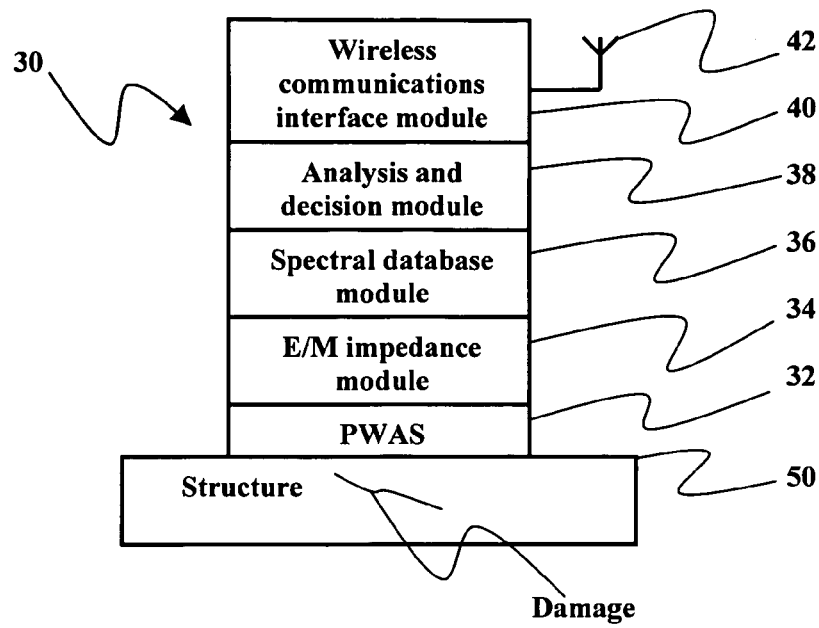
FIG. 3 schematically illustrates the functional relationship of component modules within the device in accordance with the present technology.

Reference will now be made in detail to the presently preferred embodiments of the subject self-processing integrated damage assessment sensor (SPIDAS) for structural health monitoring. Referring now to the drawings and in particular to FIG. 3 wherein is schematically illustrates the functional relationship of the various component modules within a SPIDAS device 30 in accordance with the present technology. As illustrated in FIG. 3, a SPIDAS device 30 may correspond to several interconnected modules configured together as a unitary integrated device. More particularly, a SPIDAS device 30 may correspond to the combination of a piezoelectric wafer active sensor 32, an electromechanical impedance module 34, a spectral database module 36, an analysis and decision module 38, and a wireless communications interface module 40 that may also include an antenna element 42. As illustrated in FIG. 3, SPIDAS device 30 may be secured in any appropriate manner to a structure 50 so that monitoring of the structural health of structure 50 may be provided.

In accordance with the present technology, a systematic approach to the development of the field-portable compact small-size impedance analyzer for structural health monitoring using the E/M impedance technique has been employed. The approach taken consists of several developmental stages. First, we simulate the E/M impedance technique and develop the software tools for analyzing the signal in a fast and efficient way while maintaining the desired accuracy, the objective being to obtain the complex impedance $(Z_R + iZ_I) = |Z| \angle \arg Z$ at a number of frequencies in a predetermined range. Several signal processing methods have been explored including direct signal integration, cross-correlation, and Fourier transform (DFT and FFT).

Second, we analyze the hardware issues associated with the implementation of this approach. The size of the overall system is discussed, and implementations using either a laptop computer or a digital signal processor (DSP) are considered. The system architecture consists of several blocks including reference signal generation, voltage and current measurements, and digital signal acquisition and processing.

Third, we perform a thorough calibration of our new methodology using passive components (R, C, and R-C), as well as active components (PWAS). In this calibration, we compare the results measured with our new method against the results measured with an existing laboratory-size impedance analyzer (e.g., HP4194A).

As previously mentioned with respect to FIG. 3, the self-processing integrated damage assessment sensor (SPIDAS) in accordance with the present technology consists of several modules: (a) an E/M impedance module 34 that measures the E/M impedance of the active sensors, (b) a spectral database module 36 that stores the historical data of E/M impedance spectra, (c) an analysis and decision module 38 that performs impedance spectroscopy, compares measured data with stored data, and issues structural health reports, and (d) a wireless communication interface module 40 that conditions the information signals for transmission over a wireless network. Is should be understood that although the principally illustrated signal transmission methodology corresponds to a wireless configuration, such is not limiting to the present technology, as other transmission methodologies, including wired methodologies may be used. Moreover, the designation of wireless methodologies are not limited to radio frequency transmissions, as other transmission modes including optical and ultrasonic methodologies may be used.

The E/M impedance module 34 measures the complex electrical impedance at the piezoelectric wafer active sensor (PWAS) terminals during the structural health monitoring process. Measurements may be performed in a range of frequencies as will be discussed later. The spectral database module 36 stores historical data of impedance spectra measured at the same PWAS at certain dates. The database may also store environmental conditions, as collected from environmental sensors (not shown) and transmitted through the wireless interface 40. The analysis and decision module 38 performs impedance spectroscopy, compares the measured date with the stored data, and issues structural health reports. The wireless communication interface module 40 conditions the information signals for transmission over the wireless network. Conditioning of the signal for transmission may include such features as appending location and particular sensor identifying data to the measurement data collected in addition to processing of the data for reliable transmission. The wireless communications module may also receives, via, for example, antenna 42, information from other sensors in the network, such as environmental sensors (not shown) or other PWAS devices.

Figure 4:
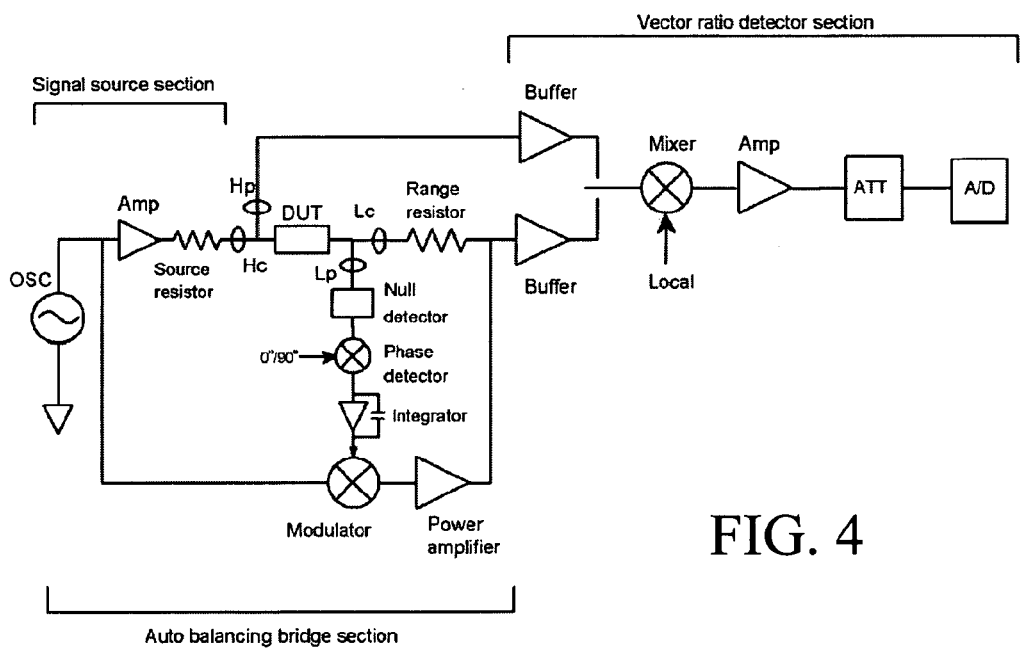
FIG. 4 illustrates a simplified block diagram of the analog section of an HP 4194A precision impedance analyzer used to demonstrate the operation of the presently disclosed technology.

Before describing in detail the SPIDAS disclosure, it may be useful to review the operation of the existing laboratory-size impedance analyzer. The HP4194A impedance analyzer is a typical laboratory impedance analyzer and is employed herein as an example to illustrate the principle of operation of the present technology. FIG. 4 shows a simplified analog-section block diagram for the HP4194A precision impedance analyzer. The measurement circuit is functionally divided into three sections. The signal source section generates the test signal applied to the unknown device. The auto balancing bridge section balances the range resistor current with the device under test (DUT) current to maintain a zero potential at the low terminal. The vector ratio detector section measures two vector voltages across the DUT (Edut) and range resistor Rr (Err) series circuit. Since the range resistor value is known, measuring two voltages will give the impedance vector Zx of the DUT by Zx=Rr×(Edut/Err).

To gradually address the issue of reducing the cost and weight, and of achieving portability, the development of the self-processing integrated damage assessment sensor (SPIDAS) concept has followed three main stages. More specifically, development has proceeded from a Desktop computer implementation to a Laptop computer implementation and finally to an embedded and wireless implementation. The portability of the impedance analyzer has improved step by step in each stage. Simultaneously, the size and cost have been reduced. Each of these stages represents an implementation option and is an important part of the overall development of the present technology.

The Desktop implementation of the self-processing integrated damage assessment sensor (SPIDAS) in accordance with the present technology utilizes standard low-cost multipurpose laboratory equipment, such as function generator, a general purpose input bus (PCI GPIB) card, a data acquisition (PCI DAQ) card, and a signal condition module (SCXI). In addition, a control program written in LabView and running on the desktop is used. As will be recognized by those of ordinary skill in the art, all the hardware components employed are compact and can be easily found in most laboratories. It should be understood that the particularly mentioned devices and programming language used are exemplary only as the use of other, equivalent devices and programming languages are clearly within the scope of the present disclosure.

As would be evident to those of ordinary skill in the art, the portability of the impedance analyzer can be improved dramatically if the desktop computer used in the initial implementation is replaced by a laptop computer. In such an implementation, the use of laptop specific data acquisition cards, a PCMCIA DAQ I/O card, for example, instead of a PCI DAQ card and a connection box for signal conditioning and amplification may be employed. Software developed for the previous Desktop concept impedance analyzer may, of course, also be used with the laptop configuration with only little adaptation.

The final aim in developing a self-processing integrated damage assessment sensor (SPIDAS) in accordance with the present technology is to achieve a self contained, unobtrusive electromechanical (E/M) impedance monitoring system. In this final development stage, all functions of the impedance analyzer are implemented on a single chip, such as digital signal processor (DSP), and combined with memory, data processing and analysis, and a wireless communication interface for efficient delivery of the health monitoring information.

Figure 5:
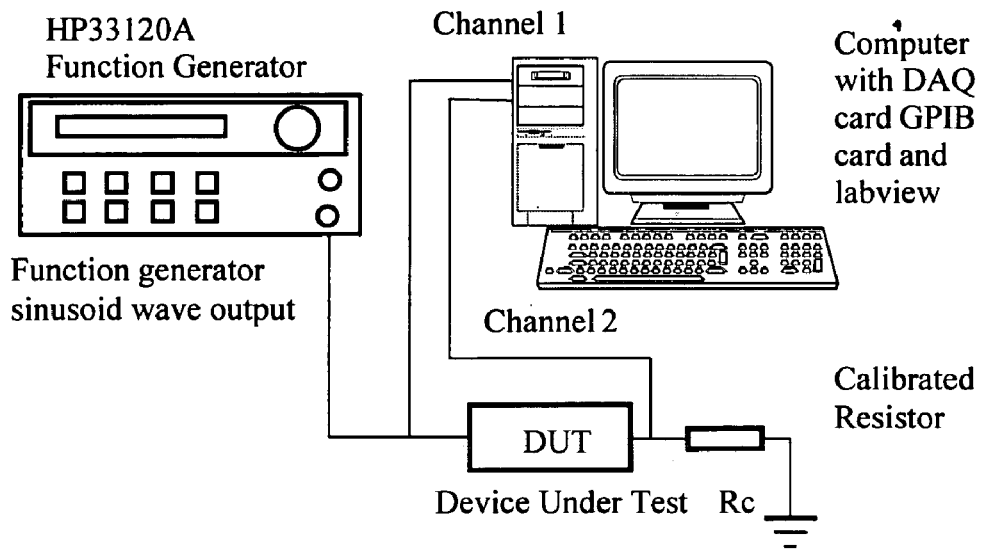
FIG. 5 illustrates an exemplary test setup useful for demonstration the operation of a device constructed in accordance with the present technology.

To verify the concept of the desktop implementation of a self-processing integrated damage assessment sensor (SPIDAS) in accordance with the present technology, a proof-of-concept demonstration using an appropriately programmed Desktop computer and employing associated data acquisition cards as illustrated in FIG. 5 was developed. In this demonstration configuration the following hardware was used:

(1) a Desktop PC Pentium III 550 computer with Windows 2000 operating system;

(2) an HP33120A function generator used to generator the input waveform to the system with frequency sweeping a given frequency range ($f_{start}$ to $f_{end}$, as an example, 100 MHz to 1 MHz);

(3) a general purpose input bus (GPIB) card connecting the function generator to the desktop PC and enabling communication there between (4) a Gage Applied 85G data acquisition (DAQ) card, with 5 GS/s maximum sampling frequency, and on board 10K points memory limitation (this device is capable of sampling two-channel analog signal simultaneously);

(5) a calibrated resistor, $R_c$; and (6) the device under test (DUT).

Various elements and combination including a resistor, a capacitor, a resistor-capacitor series circuit, and a piezoelectric wafer active sensor (PWAS) were used as the device under test (DUT) to demonstrate the concepts associated with the present technology.

The particular program controlling the demonstration system was developed using NI Labview 6.1, however the use of such specific programming language is only exemplary as the use of other such languages or also the use of hardware or combination of hardware and software are also contemplated. In the exemplary demonstration configuration, the control software included three main modules and an error handling mechanism:

(1) an Input module, which sets up the system input variables, such as the start and the end values of the sweeping frequency range;

(2) a DAQ control module, which sets up the sampling frequency and the number of data points to be captured and stores the data;

(3) a Data analysis module, which analyzes the sampled data using the FFT algorithm to extract the DUT impedance and also plots the results; and (4) an error handling mechanism, which reports an error when the input parameters are not properly setup, the power of the function generator is not on, or upon the occurrence of other errors.

The demonstration system may be configured with a graphical user interface (GUI) as a portion of the operating software. The GUI permits a user to easily select or enter desired operational or test parameters such as the start sweeping frequency, end sweeping frequency, number of frequency point and digital frequency. The user may also select the impedance output mode and then have the software operate the computer and associated equipment to perform a test run and collect and save test data. Following a test run, the data are processed and displayed as impedance curves within a window of the GUI. The data may also be stored in "csv" or other appropriate file format for post-processing in other software codes and/or programs(e.g., Microsoft Excel).

Figure 6:
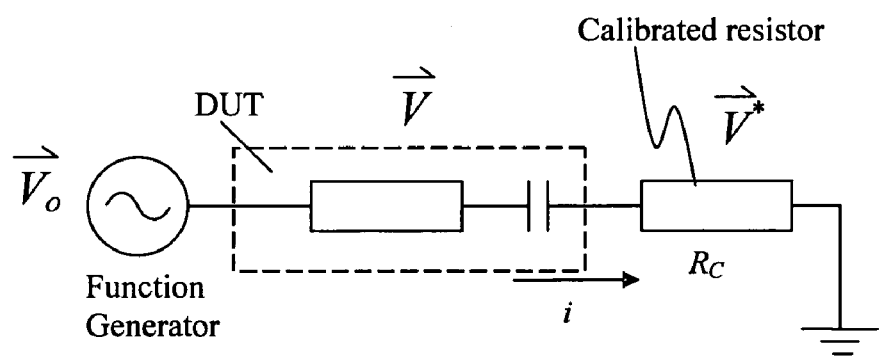
FIG. 6 illustrates a schematic diagram of a circuit used to explain the impedance measuring principle employed in the present technology.

The circuit illustrated in FIG. 6 used to measure the device under test (DUT) electrical impedance is similar to a voltage divider. The function generator sends an input signal $\sqrt{V}_0$ that in an exemplary configuration may be sinusoidal in form with a frequency f that varies in a given frequency range from a start frequency $f_{start}$ to en end frequency $f_{end}$. In an exemplary concept demonstration the start and end frequencies corresponded to 100 KHz and 1 MHz, respectively. The current i flowing through the DUT also flows through the known low-value calibrated resistor $R_c$. In the exemplary concept demonstration $R_c$ was selected to be 10 Ω. The current is calculated using the voltage $\sqrt{V}^*$ measured across the calibrated resistor $R_c$.

$$i = \frac{\vec{V}^*}{R_C} \quad (1)$$

$$Z = \frac{\vec{V}}{i} \quad (2)$$

where, Z is the impedance of DUT, i is the current, $\sqrt{V}^*$ is the voltage across resistor $R_c$, and $\sqrt{V}$ is the voltage across the DUT. From Equations (1) and (2) we obtain:

$$Z = \frac{\vec{V}}{\vec{V}^*} R_C \quad (3)$$

Equation (3) shows that the voltages $\sqrt{V}$ and $\sqrt{V}^*$, across the DUT and the calibrated resistor, should be measured simultaneously and, for this demonstration, the Gage Applied DAQ card employed has two A/D channels to accommodate this requirement. The voltages $\sqrt{V}$ and $\sqrt{V}^*$ could, however, be measured directly on these two channels using two differential probes, but as differential probes are expensive, we chose to measure the voltage across the DUT in an indirect way by subtracting the voltage across the calibrated resistor, $\sqrt{V}^*$, from the input voltage received from the function generator, $\sqrt{V}_0$.

Equation (3) indicates that $\sqrt{V}$ and $\sqrt{V}^*$ are phasors, which can be easily processed in complex numbers format. In order to derive the impedance Z of Equation (3), we need to calculate the amplitude ratio and the phase difference between $\sqrt{V}$ and $\sqrt{V}^*$. Of these two, the phase difference is more difficult to ascertain. Several methods are available for measuring the phase difference between two sinusoidal signals, including as non-limiting examples zero crossing, signal integration (the technique used by an HP4194A analyzer), cross-correlation, and Fourier Transform. After preliminary testing, the Fourier Transform method was adopted because it offers speed and accuracy.

As an illustration of the concepts embodied in the present technology, consider a harmonic signal:

$$x_1(t) = A \sin(2\pi f t) \tag{4}$$

where, A is the signal amplitude and f is the signal frequency. After sampling, the digitized signal of $x_1(t)$ is $x_1(n)$ given by:

$$x_1(n) = A \sin(2\pi f n T_S) = A \sin(2\pi n f/f_S) = A \sin(2qn/N),$$
$$n = 0, 1, 2, \ldots, N-1 \tag{5}$$

where, $q = fN/f_S$, N is the number of sampled data points, $f_S$ is the sampling frequency, $T_S$ is the sampling time interval, $T_S = 1/f_S$. The Discrete Fourier Transform (DFT) of $x_1(n)$ is given by:

$$X_1(K) = \sum_{n=0}^{N-1} x(n) e^{-j(2\pi/N)Kn} \tag{6}$$

$$= \sum_{n=0}^{N-1} A \sin(2qn/N) \cdot e^{-j(2\pi/N)Kn}$$

$$= A \frac{j}{2} \sum_{n=0}^{N-1} [e^{-j2\pi(q+K)n/N} - e^{-j2\pi(q-K)n/N}]$$

Where, K = 0, 1, 2, ..., N−1, and $j = \sqrt{-1}$. Note that:

$$\begin{cases} K \neq q, \; N-q; \; X_1(K) = 0 \\ K = q, \; N-q; \; X_1(K) = -\frac{A}{2} N j \end{cases} \tag{7}$$

Equation (7) allows calculation of the signal amplitude, A.

Now consider a harmonic signal with phase θ, i.e., $$x_2(t) = A \sin(2\pi f t + \theta) \tag{8}$$

where θ is the initial phase of the signal. Performing the DFT of $x_2(t)$ gives:

$$X_2(K) = A \frac{j}{2} e^{j\theta} (e^{-j2\pi(q+K)n/N} - e^{-j2\pi(q-K)n/N}), \tag{9}$$
$$K = 0, 1, 2, \ldots, N-1$$

Note that:

$$\begin{cases} K \neq q, \; N-q; \; X_1(K) = 0 \\ K = q, \; N-q; \; X_1(K) = X(K) = \frac{A}{2} N \sin\theta - j\frac{A}{2} N \cos\theta \end{cases} \tag{10}$$

Equation (10) allows us to calculate the signal amplitude, A, and phase, θ.

In order to demonstrate the effectiveness of the new method in taking impedance measurements, four experiments were performed using a proof-of-concept demonstrator in comparison with the HP4194A laboratory impedance analyzer. Four separate devices/combinations were used in these experiments including a resistor, a capacitor, a series resistor-capacitor circuit and a piezoelectric wafer active sensor (PWAS). The measured results are presented in comparison with those measured with the HP4194A laboratory impedance analyzer in FIGS. 7a, 7b, 8, 9a, 9b, 10a, and 10b, respectively.

Figure 7A:
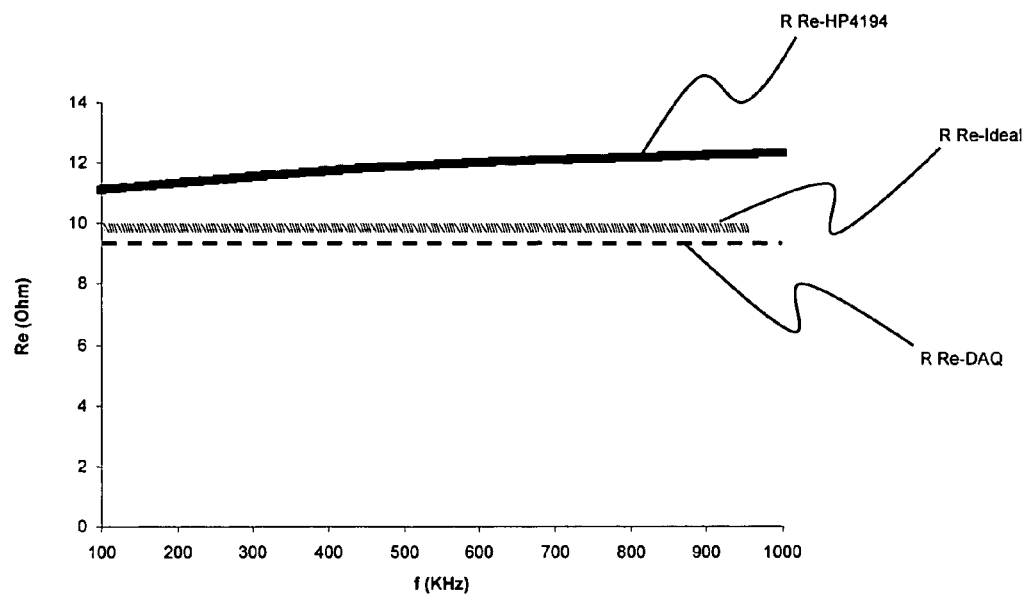
FIGS. 7a and 7b graphically illustrate impedance curves corresponding to the results of tests using a resistor to demonstrate concepts involved with the present technology.
Figure 7B:
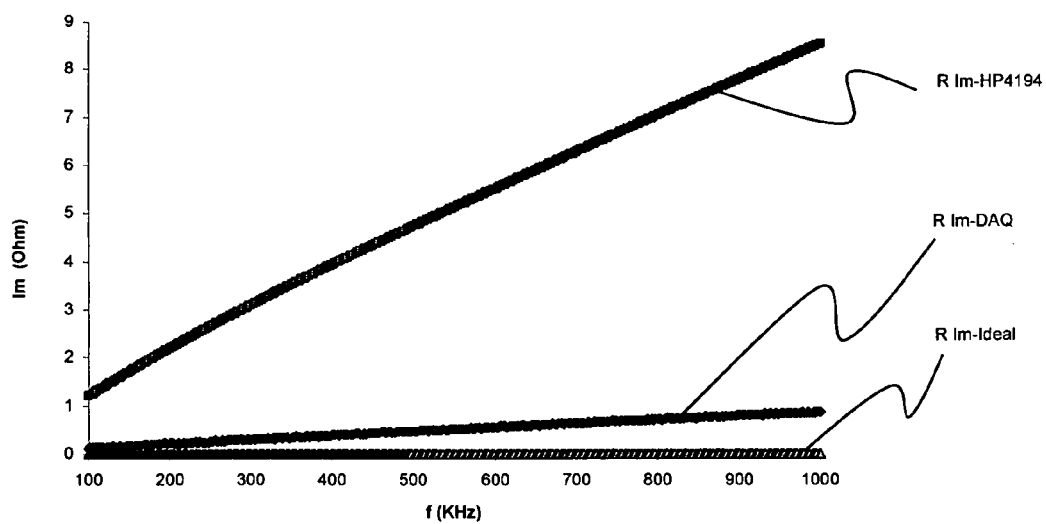

In the first example, a resistor with a value of 9.8 Ω was measured with the proof-of-concept demonstrator and an HP4194 impedance analyzer. The results are compared with ideal resistor impedance curves in FIG. 7a. The real part of the ideal resistance should be 9.8 Ω, while the imaginary part should be zero. However, due to parasitic effects, the imaginary part does not show exactly zero. Examination of FIG. 7b shows that the proof-of-concept demonstrator has a better result than the HP4194 impedance analyzer when measuring imaginary part of resistor.

Figure 8:
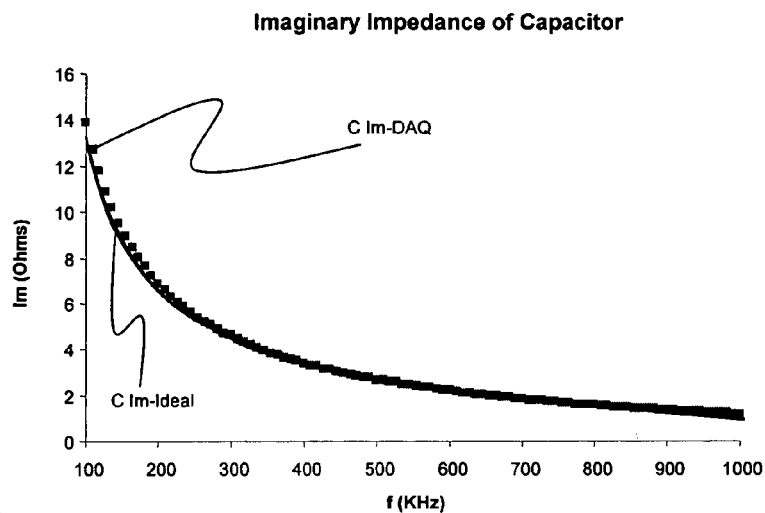
FIG. 8 graphically illustrates impedance curves corresponding to the results of tests using a capacitor to demonstrate concepts involved with the present technology.

Next, a capacitor with the value of 0.1 µF was measured with the proof-of-concept demonstrator. The results are plotted in FIG. 8. Also plotted are the results predicted with the formula $$Z = \frac{1}{i\omega C} \tag{11}$$

where $i = \sqrt{-1}$. Examination of FIG. 8 shows that very little difference is apparent between the measured and theoretical curves.

In a third experiment, measurements were made with a resistor and capacitor in series (R=10 Ω, C=0.01 µF). The equivalent impedance is given by:

$$Z = R + \frac{1}{i\omega C} \tag{12}$$

Figure 9A:
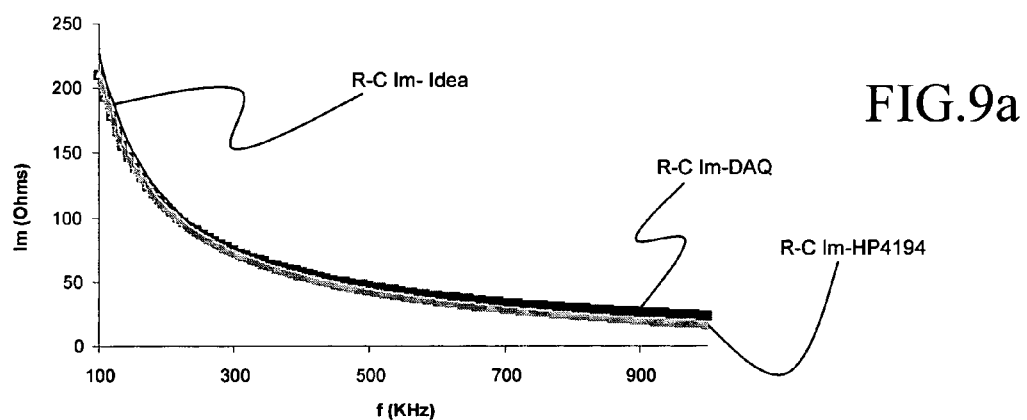
FIGS. 9a and 9b graphically illustrate impedance curves corresponding to the results of tests using a resistor/capacitor combination to demonstrate concepts involved with the present technology.
Figure 9B:
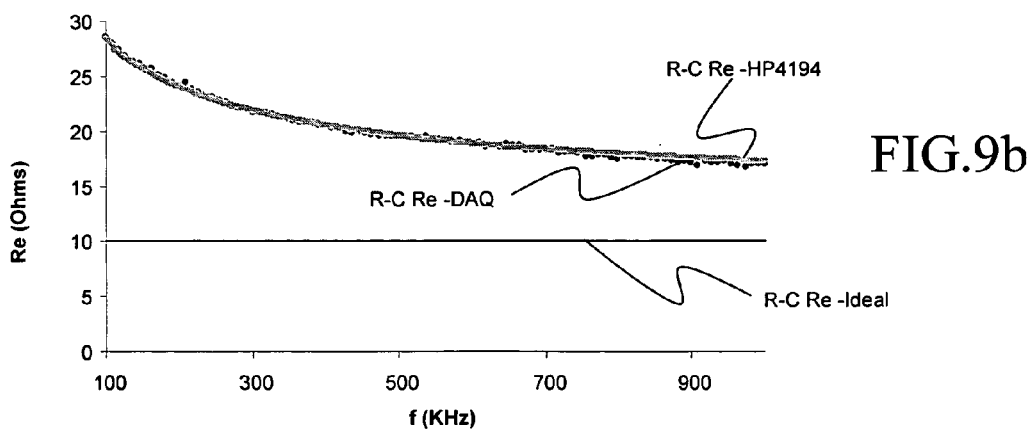

Measurements were made with the proof-of-concept demonstrator and an HP4194A laboratory impedance analyzer. As indicated in FIG. 9a, the device is dominated by the imaginary part, $(i\omega C)^{-1}$. The measurements performed with the proof-of-concept demonstrator and the HP4194A are almost identical. For the imaginary part (FIG. 9b), the measured results also agree very well with the theoretical prediction of Equation (12). Although the real part (FIG. 9a) does not agree exactly with the theory of Equation (12), the agreement between proof-of-concept demonstrator and the HP4194A is also excellent. This exercise indicates that the disagreement between theory and measurements has a physical nature, and does not depend on the measuring device.

Figure 10A:
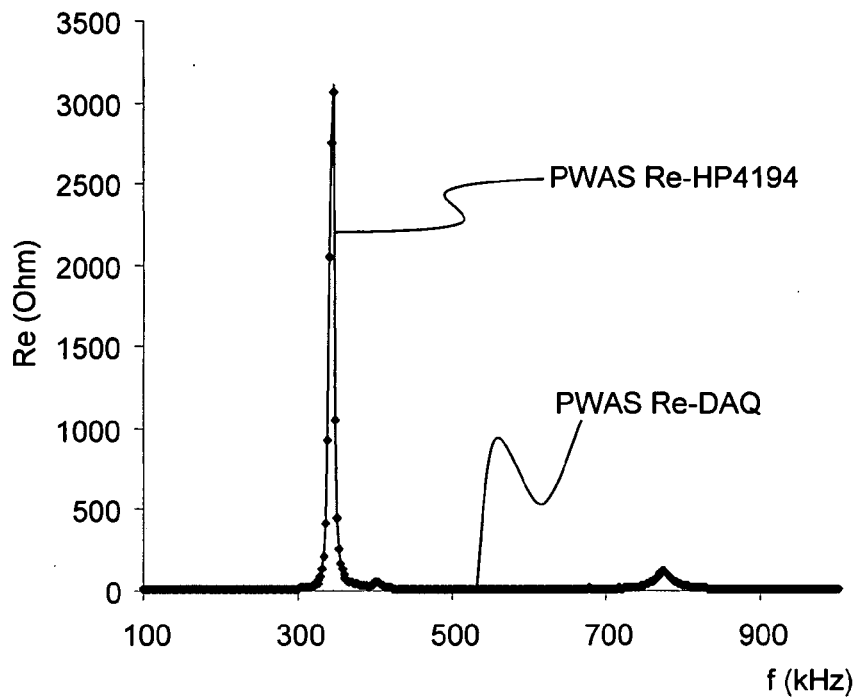
FIGS. 10a and 10b graphically illustrate impedance curves corresponding to the results of tests using a piezoelectric wafer active sensor to demonstrate concepts involved with the present technology.
Figure 10B:
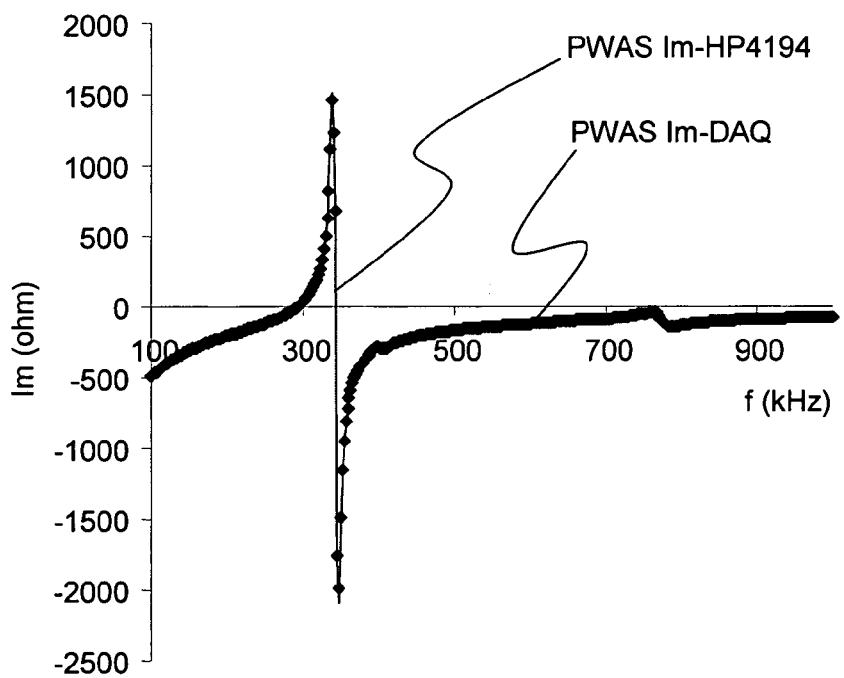

Finally, piezoelectric wafer active sensors (PWAS) were also measured. Due to the piezoelectric coupling between the electrical and mechanical energies, PWAS are active devices, i.e., they present electromechanical resonance. At resonance, the real part of the impedance goes through a peak, while the imaginary part of the impedance goes through zero. When mechanically free, the 7-mm diameter PWAS used in this experiment has its first in-plane resonance at around 350 kHz. FIG. 10a shows superposed the results measured with the proof-of-concept demonstrator and the HP4194A laboratory impedance analyzer. The two measurements are practically indistinguishable. As it is expected that the self-processing integrated damage assessment sensor (SPIDAS) of the present technology will be mainly used for structural health monitoring in conjunction with piezoelectric wafer active sensors (PWAS), the results presented in FIGS. 10a and 10b quite adequately demonstrate the effectiveness of the concepts involved with the present technology.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A self-processing integrated damage assessment sensor system comprising:
    a sensor for producing signals responsive to structural anomalies;
    a database module for storing data representative of the signals produced by said sensor;
    an analysis module responsive to signals from said sensor and data stored in said database module for producing results describing the structural anomalies sensed by said sensor; and
    a communications module for transmitting signals based at least in part on the signals produced by said analysis module,
    wherein said sensor, said database module, said analysis module and said communications module are commonly housed.

2. The self-processing integrated damage assessment sensor system of claims 1, wherein said sensor comprises a passive device.

3. The self-processing integrated damage assessment sensor system of claim 2, wherein said sensor is selected from the group consisting of resistors, capacitors, and resistor-capacitor series combinations.

4. The self-processing integrated damage assessment sensor system of claim 1, wherein the sensor comprises an active device.

5. The self-processing integrated damage assessment sensor system of claim 4, wherein the sensor comprises a piezoelectric device.

6. The self-processing integrated damage assessment sensor system of claim 5, wherein the sensor comprises a piezoelectric wafer active sensor.

7. The self-processing integrated damage assessment sensor system of claim 1, further comprising:
    an electromechanical impedance module configured to receive signals from said sensor, to measure a local impedance spectrum over a preselected range of frequencies, and to provide measurement data for use by said analysis module.

8. The self-processing integrated damage assessment sensor system of claim 7, wherein said database module comprises a spectral database module comprising a memory configured to receive measurement data from said electromechanical impedance module.

9. The self-processing integrated damage assessment sensor system of claim 1, wherein said communication module comprises a wireless interface module configured to transmit signals identifying selected of the signal source and signal location.

10. A method of assessing structural health using a self-contained integrated sensor system, comprising the steps of:
    providing a sensor for producing signals;
    measuring impedance spectra over a selected frequency ranged based on the signals;
    storing data based on said step of measuring;
    analyzing the measured impedance spectra to determine the presence of preselected selected signal characteristics indicative of structural health;
    providing selected of said data as a portion of the measured impedance spectra in the step of analyzing; and
    producing signals indicative of anomalies in structural health.

11. The method of claim 10, further comprising the step of transmitting signals based at least in part on the results of the step of analyzing.

12. The method of claim 10, further comprising the step of wirelessly transmitting signals based at least in part on the results of the step of analyzing.

13. The method of claim 10, wherein the step of providing a sensor comprises providing a passive sensor.

14. The method of claim 10, wherein the step of providing a sensor comprises providing an active sensor.

15. The method of claim 14, wherein the step of providing an active sensor comprises providing a piezoelectric wafer active sensor.

* * * * *

UNITED STATES PATENT AND TRADEMARK OFFICE
CERTIFICATE OF CORRECTION

| | |
|---|---|
| PATENT NO. | : 7,174,255 B2 |
| APPLICATION NO. | : 10/987765 |
| DATED | : February 6, 2007 |
| INVENTOR(S) | : Victor Giurgiutiu and Buli Xu |

Page 1 of 1

It is certified that error appears in the above-identified patent and that said Letters Patent is hereby corrected as shown below:

Column 11, line 34 (Claim 2), "...system of claims 1," should be --...system of claim 1,--

Signed and Sealed this

Third Day of July, 2007

JON W. DUDAS
*Director of the United States Patent and Trademark Office*